United States Patent [19]

Pinto et al.

[11] 4,172,149

[45] Oct. 23, 1979

[54] METHOD FOR TREATING LIVING SKIN EXHIBITING EXCESSIVE SEBUM SECRETION

[75] Inventors: Jeffrey S. Pinto, East Aurora, N.Y.; Sung L. Hsia, Miami, Fla.; Paul L. Warner, Jr., Clarence, N.Y.

[73] Assignee: Westwood Pharmaceuticals, Inc., Buffalo, N.Y.

[21] Appl. No.: 873,320

[22] Filed: Jan. 30, 1978

[51] Int. Cl.$^2$ .............................................. A61K 31/23
[52] U.S. Cl. .................................. 424/312; 424/311; 424/313
[58] Field of Search ................ 424/311, 312, 314, 313

[56] References Cited

U.S. PATENT DOCUMENTS

| 3,577,516 | 5/1971 | Gould et al. | 424/46 |
| 3,948,943 | 4/1976 | Eberhardt et al. | 260/326.45 |
| 3,949,087 | 4/1976 | Bacq et al. | 424/319 |
| 3,984,535 | 10/1976 | Ghilardi et al. | 424/47 |
| 4,016,287 | 4/1977 | Eberhardt et al. | 424/309 |

*Primary Examiner*—Leonard Schenkman
*Attorney, Agent, or Firm*—Morton S. Simon; Irving Holtzman

[57] ABSTRACT

Treats living skin in which sebum secretion is excessive with certain triglycerides to reduce the level of sebum secretion.

14 Claims, 4 Drawing Figures

THIN LAYER CHROMATOGRAPHY OF RAT SKIN LIPIDS

METHOD FOR TREATING LIVING SKIN EXHIBITING EXCESSIVE SEBUM SECRETION

This invention relates to a method for treating living skin in which there is an excessive secretion of sebum. It concerns, for example, the treatment of a group of skin diseases that are associated with seborrhea and generally characterized by an excessive secretion of sebum, which collects on the skin in the form of an oily coating often accompanied by crusts or scales. Moreover, the invention is also applicable to other skin conditions in which the excessive secretion of sebum is only one component of the pathology. The latter case may be exemplified by such skin conditions as acne vulgaris, acne rosacea and seborrheic dermatitis.

Traditionally, attempts have been made to counteract excessive sebum production through frequent washing with soap or detergent scrubs. This, however, has not proven to be very satisfactory. Moreover, it has been suggested that skin greasiness could be reduced by controlling the rate of sebum secretion through diet or hormonal manipulation. This also has met with only very limited success.

In addition, efforts have been made to control the greasiness of skin by the use of topically applied agents. An example of the above is described in U.S. Pat. No. 3,948,943 in which the patentees suggest the use of certain heterocyclic aminocarboxylic acid higher alkylamides for inhibiting sebaceous gland secretion. A further example is described in U.S. Pat. No. 3,984,535 which teaches the use of 2,6-di. tert. butyl paracresol, propyl gallate, butyl hydroxy anisol, octyl gallate or dodecyl gallate in a carrier as a scalp deodorant, and claims that these compositions cause a significant reduction of sebum. Other examples are U.S. Pat. Nos. 4,016,287 and 3,949,087; the former claiming inhibition of sebaceous gland excretion by the topical use of the compound N-(4'-phenyl-benzoyl)-4-amino-butyric acid and the latter, the topical use of d,l-carnitine chloride or l-carnitine chloride, or a mixture of both for the suppression of seborrhea.

It has now been found that sebum production in the living skin can be controlled by controlling the synthesis of the triglycerides, the major components of sebum. More particularly, it has been found that certain fatty acid triglycerides, described in more detail below, are effective blocking agents in the biosynthesis of the sebum triglycerides in the skin. Consequently, they may be employed as topical agents for the management of skin conditions characterized by the over production of sebum.

It is accordingly an object of the present invention to provide a process for reducing the excessive secretion of sebum in living skin.

It is also an object of the present invention to provide a process for treating diseases of the skin in which at least one of the pathological conditions of the disease is an excessive secretion of sebum.

Other and more detailed objects of this invention will be apparent from the following description and claims.

Figure 1:
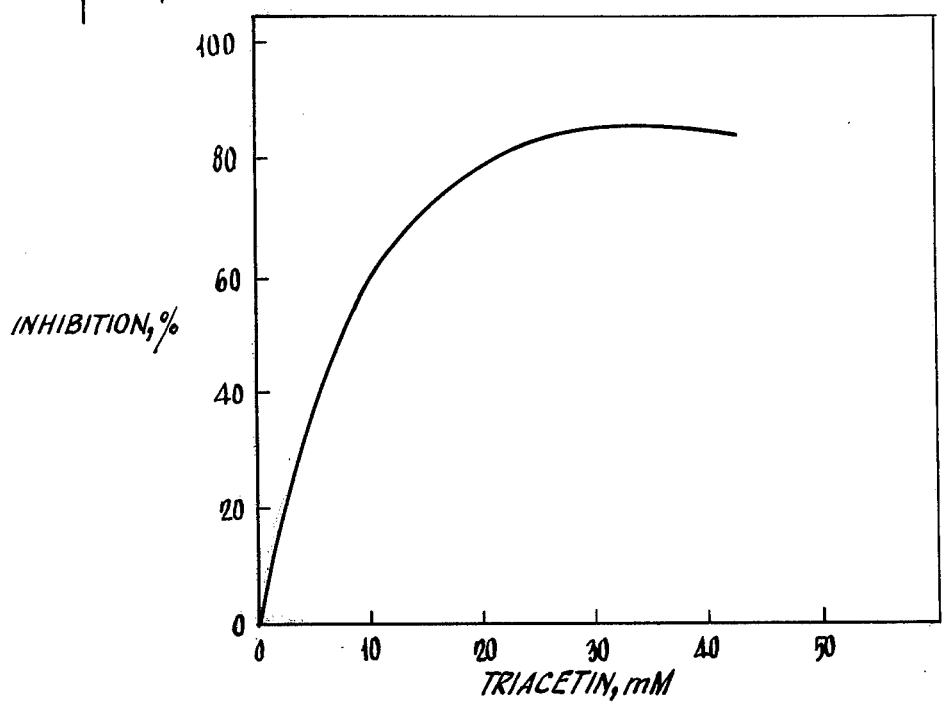
FIG. 1 is a graph summarizing a study showing the percent inhibition of tripalmitin production for excised human skin containing sebaceous glands when incubated with a medium containing [8,9-$^3$H] palmitic acid and triacetin.

The triglycerides that may be used in accordance with the present invention may be described by the general formula:

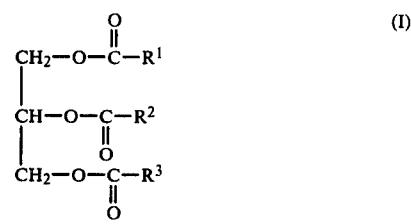

wherein $R^1$, $R^2$ and $R^3$ are straight chain, branched chain, saturated or unsaturated aliphatic hydrocarbon radicals having from 1 to 20 carbon atoms. $R^1$, $R^2$ and $R^3$ may be the same or a different aliphatic hydrocarbon radical but they most often will be the same radical. In the preferred form of the invention, $R^1$, $R^2$ and $R^3$ represent the same alkyl group and usually a saturated alkyl group having from 1 to 9 carbon atoms. The acyl portion of the triglycerides of Formula I above i.e.

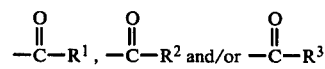

can be derived from a variety of fatty acids. These preferably include such fatty acids having 2 to 10 carbon atoms and particularly acetic acid, n-propionic acid, n-butyric acid, valeric, caproic, enanthylic, caprylic, pelargonic and capric acids. Illustrative of other saturated fatty acids and unsaturated fatty acids that may serve as the source for the acyl radicals

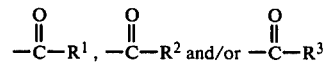

mention may be made of lauric, myristic, palmitic, stearic and arachidic, $\Delta^9$-decylenic, $\Delta^9$-dodecylenic, palmitoleic, oleic, linoleic, linolenic, gadoleic and arachidonic acids. As examples of branched chain triglycerides that may be used in the present invention, mention may be made of isotributanoin, anteisotrioctanoin, isotrihexanoin, anteisotrihexanoin, isotridecanoin, and anteisotridecanoin. In accordance with this invention, single triglycerides or mixtures of triglycerides may be employed for the present purposes. When a mixture of triglycerides is employed, each of $R^1$, $R^2$ and $R^3$ is preferably saturated alkyl having 3 to 9 carbon atoms or a radical containing 7 to 10 carbon atoms. Also preferred are triglycerides wherein $R^1$, $R^2$ and $R^3$ each have from 10 to 20 carbon atoms.

As indicated, the aforesaid triglycerides may be applied to oily living skin i.e. skin in which there is an excessive secretion of sebum to retard the biosynthesis of sebum triglycerides. This process involves coating the skin area which exhibits an excessive rate of sebum production with a triglyceride product comprising at least about 10% and preferably at least 50% by weight of one or more triglycerides of Formula I up to about 100% by weight of said triglycerides. This is applied in repeated applications over a period of time sufficient and in an amount sufficient to materially reduce the rate of sebum production. These triglycerides may be applied as such in which event they will comprise about 100% by weight of the triglyceride product. They may also be distributed in a pharmaceutically acceptable vehicle. In this case, triglyceride or triglycerides will comprise about at least 10% by weight of the triglyceride product and preferably at least 50%.

For the best results, the triglyceride products of the present invention are applied periodically over a period of time. This will vary with the particular triglyceride or triglycerides that are employed. However, generally an application of the product of at least once a day over a period of about at least 9 or more days will suffice to get the desired results. The treatment will usually continue until the rate of sebum production is reduced to an acceptable level.

The quantity of product to be applied during any one day to get effective results also varies and depends on the particular triglyceride that is selected for use. For example, with tricaprylin, a 34.9% reduction of neutral lipid is seen with doses as low as 0.5 gm/70 cm$^2$/day for a period of 14 days whereas with tributyrin at a dose of 2 gm/70 cm$^2$/day for 14 days the reduction is only 10.4%. Other triglycerides tested showed an effective dosage level within this range.

The effectiveness of treatment has been shown to be dose dependent when tricaprylin was applied topically in a range of 0.5–2 gm/70 cm$^2$/day for 14 days. The reduction in sebum production was 34.9% at 0.5 gm/day, 42.5% at 1 gm/day and 47.3% at 2 gm/day.

The upper limit to the quantity of triglyceride that is to be applied on a daily basis is not critical and depends on factors such as the economics and the elegance of the treatment involved. The blocking effect of the triglycerides appears to increase with the increase in the daily quantity of triglyceride applied. In the upper ranges, as much as 6 gm/day can be employed as an effective lipogenic blocking agent when applied to a living skin area of from about 60 to 75 square centimeters.

The blocking agents described in Formula I above will ordinarily be used in conjunction with a pharmaceutical vehicle. Thus, it will usually be applied in the form of simple solutions, lotions, creams, ointments, etc. A typical composition will contain the active blocking agent in a vehicle in a concentration in the range of from about 10% to 90% by weight based on the total weight of the composition and preferably between about 50% and 90%. Conventional aids ordinarily employed in formulating lotions, creams, ointments and gels such as mineral oil, petrolatum, propylene glycol, stearyl alcohol, sodium lauryl sulfate, carbopol, triethanolamine, water, ethanol, polyethylene glycol may also be incorporated in the composition of the present invention.

The following Examples are given to further illustrate the present invention. It is understood, however, that the invention is not limited thereto.

EXAMPLE 1

Human facial skin was obtained from plastic surgery. Dermis rich in sebaceous glands was prepared after the epidermis was removed with a keratome set at 0.2 mm, and the subcutaneous fat was trimmed off with a pair of scissors. The preparation was cut into squares of 1 cm$^2$. Each square was incubated at 37° C. for 2 hours with either 5$\mu$ Ci of [8,9-$^3$H] palmitic acid (0.2 mM) or 5$\mu$ Ci of [U-$^{14}$C] glucose in a medium consisting of 1 ml Krebs-Ringer bicarbonate buffer containing 5.5 mM glucose, 4% bovine serum albumin, gassed to pH 7.4 under $O_2:CO_2$ (95:5) with or without triacetin (4.5 to 41 mM). At the end of the incubation, the tissue was removed from the incubation medium, rinsed three times with saline and homogenized in 3 ml of chloroform methanol (2:1). The lipid extract was subjected to TLC developed sequentially in ethyl ether:benzene:acetic acid: ethanol (40:50:0.2:2) and ethyl ether-hexane (6:94). Radioactivity in the triglyceride fraction was assayed by scintillation counting. Inhibition of triglyceride synthesis was expressed as a percentage of the control value (without inhibitor). The results are shown in FIGS. 1 and 2.

In FIG. 1 the results are summarized for the experiments in which [8,9-$^3$H] palmitic acid was contained in the incubation medium. The percent inhibition of tripalmitin production is plotted against the concentration of triacetin contained in the incubation medium. This demonstrates the inhibition on the formation of tripalmitin from [8,9-$^3$H] palmitic acid by triacetin. The results are obtained by comparing the level of tripalmitin obtained in the control incubation experiments (no triacetin) with that obtained in the experiments that employ various concentrations of triacetin in the incubation medium (4.5 to 40 mM).

Figure 2:
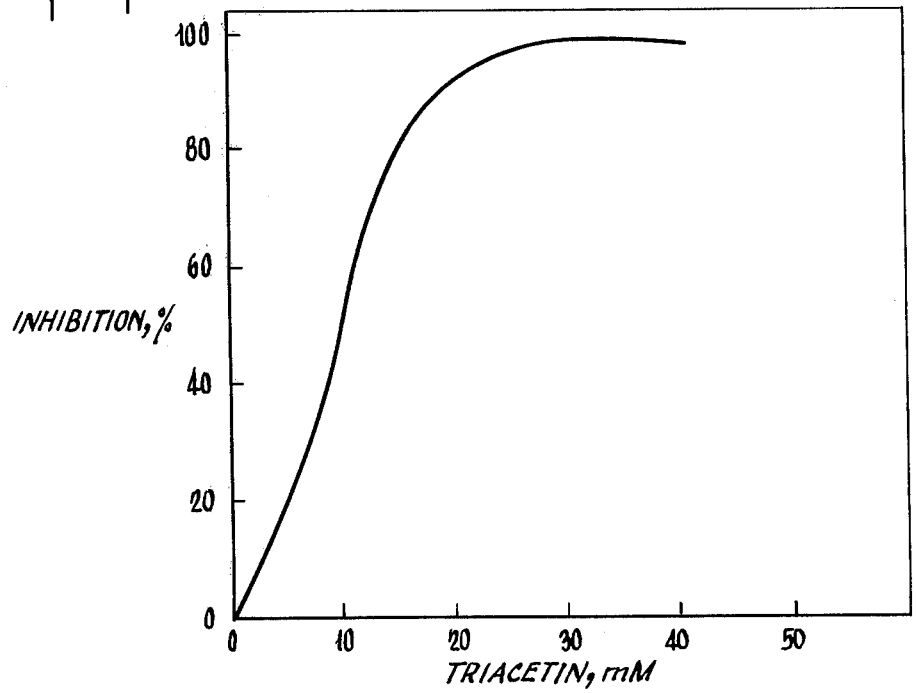
FIG. 2 is a graph summarizing a study showing the percent inhibition of tripalmitin production for excised human skin containing sebaceous glands when incubated with a medium containing [U-$^{14}$C] glucose and triacetin.

In FIG. 2 the results are summarized for the experiments in which [U-$^{14}$C] glucose is contained in the incubation medium. Here again, the percent inhibition of tripalmitin production is plotted against the concentration of triacetin in the incubation medium. In this case, however, the effect of triacetin was calculated on the basis of the $^{14}$C incorporated in the triglyceride fraction. FIG. 2 demonstrates the inhibition on the formation of tripalmitin from [U-$^{14}$C] glucose by triacetin. As in the case with FIG. 1, the results are obtained by comparing the level of tripalmitin obtained in the control experiment (no triacetin) with that obtained in the experiments that use various concentrations of triacetin (4.5 to 40 mM).

It is to be noted that in each case a dose response curve is obtained. That is to say, that the percent inhibition of tripalmitin production increases with a corresponding increase in the concentration of the triacetin in the incubation medium.

EXAMPLE 2

Male Spraque-Dawley rats weighing 250–350 g were fed Purina Rat Chow ad lib and kept in individual cages. On day 0, the hair on the back of the animals was clipped with a hair clipper, and the back was washed with hexane. The animals were then divided into two groups. Group A were controls and were not treated with any topical agent. Group B were treated topically, once each day, with glyceryl triacetate (triacetin). The amount of triacetin applied was 400 $\mu$l to an area of approximately 77 cm$^2$ on the back where the hair had been clipped. On day 4 and day 9, six or seven animals from each group were killed by asphyxiation in $CO_2$. The skin on the back was immediately removed and mounted on a lipid extractor.

The skin lipids were first extracted with 10 ml of hexane six times. The extracts were pooled and filtered to remove the dirt and tissue debris, and evaporated to dryness in a tared aluminum planchet. The weight of the residue was determined on an analytical balance. The hexane extract contains mostly triglycerides.

The skin was then extracted six times with 10 ml of $HCCl_3$:MeOH (2:1) and the weight of the residue from this extract was also determined gravimetrically. In previous experiments, it was found that six extractions with these solvents exhaustively removed the lipids on the skin under the stated conditions.

For further analysis of the lipids extracted from rat skin, aliquots of the lipid residues were applied to thin layer plates of Silica Gel G, which were developed in the solvent system of benzene:ethyl acetate:ether:acetic acid (80:10:10:0.2, v/v) according to Storry and Tuckley (Lipids 2:501, 1967). The lipids were visualized by a spray of phosphomolybdic acid.

Figure 3:
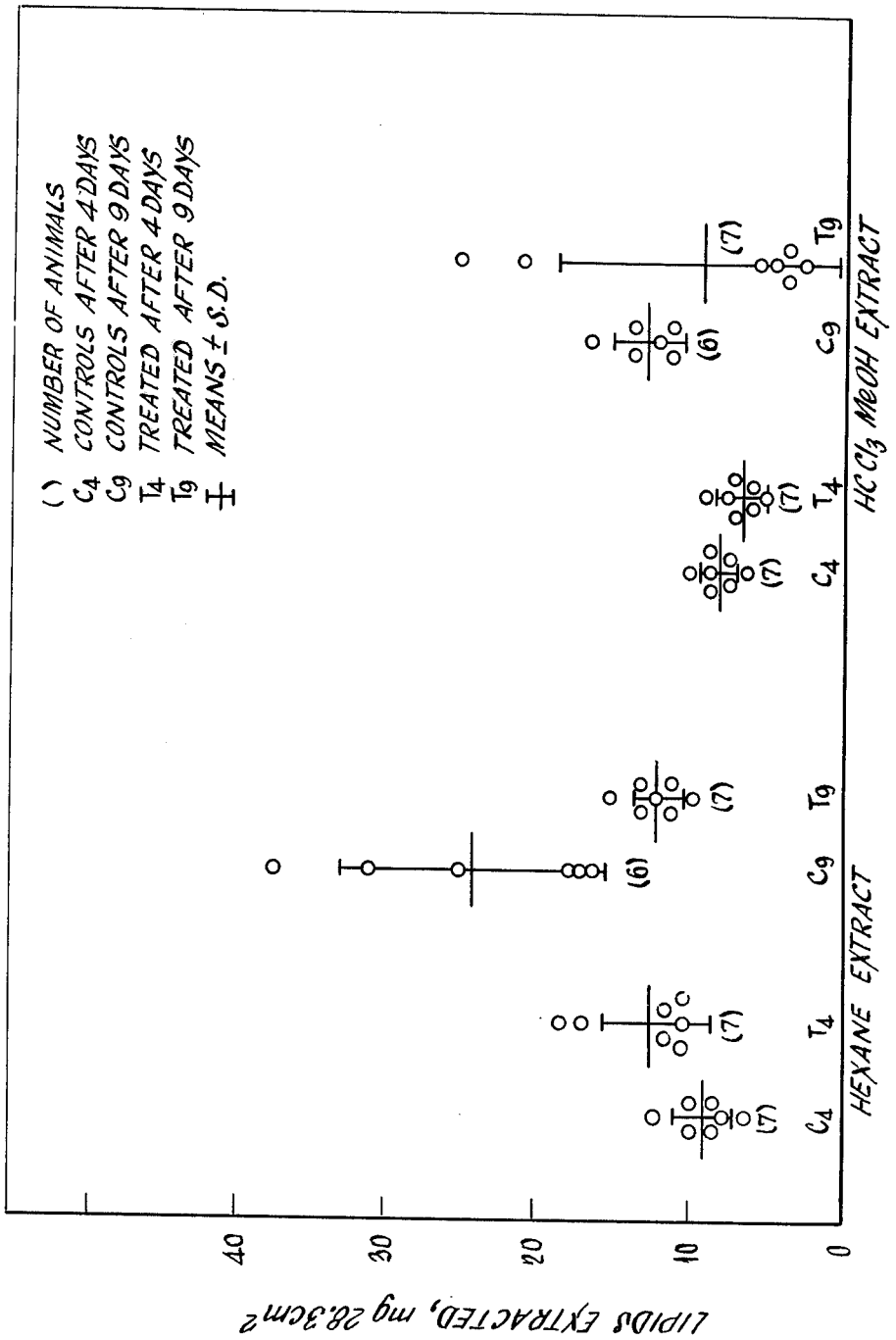
FIG. 3 is a graph summarizing a study showing the reduction of rat skin lipids after topical application of triacetin in accordance with the present invention.

FIG. 3 shows the weights of lipids extracted from the skin of control rats and rats treated topically with triacetin. It is seen that after 4 days of treatment, there was no significant difference between the weights of the lipids extracted from the surface of the skin of the two groups of animals. Clear differences were, however, observed after 9 days of treatment. The reduction in skin surface lipids of the treated animals was about 50%. The amount of lipids from the treated animals practically remained the same on day 9 as on day 4, while from day 4 to day 9 the lipids from the controls more than doubled. A 5 μl aliquot of the residue from the hexane extract (dissolved in 1 ml of hexane), and a 10 μl aliquot of the residue from the $HCCl_3$:MeOH (2:1) extract (dissolved in 1 ml of $HCCl_3$:MeOH) were applied to thin layer plates.

Figure 4:
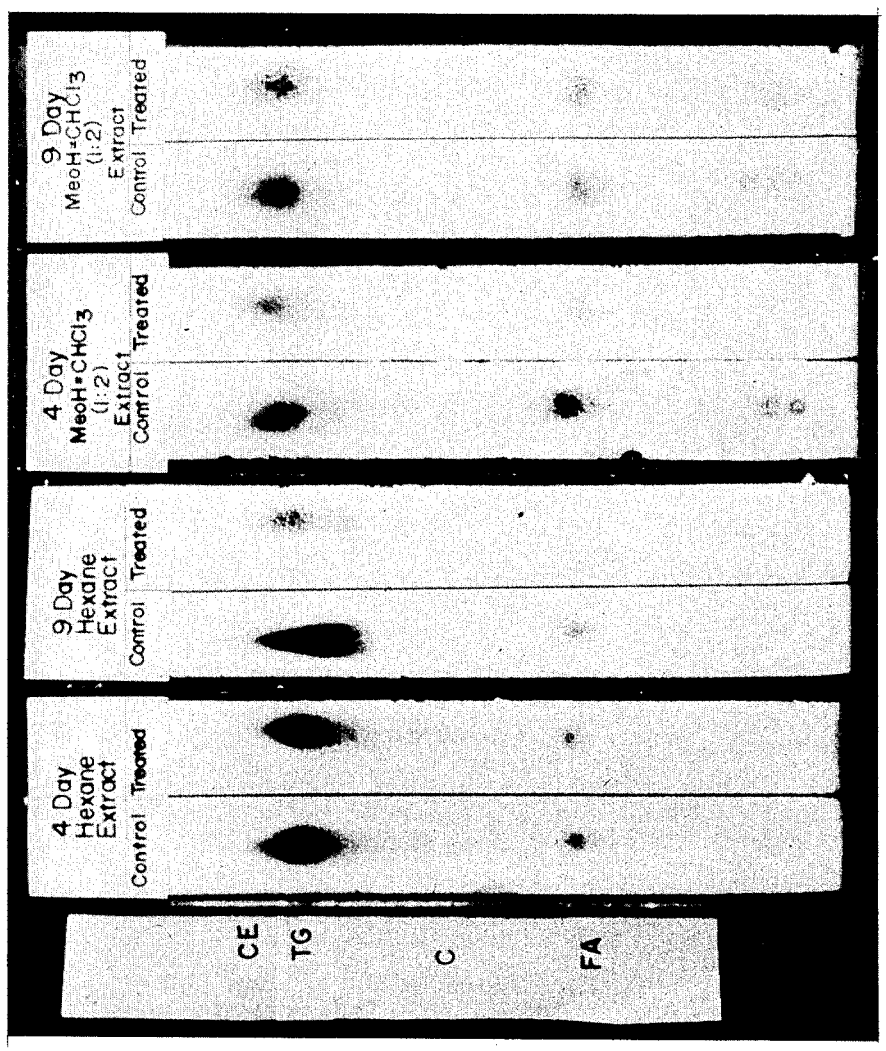
FIG. 4 is a copy of a thin layer chromatograph showing the separation of the fractions contained in extracts from skin that was treated and skin that was untreated with triacetin in accordance with the present invention.

FIG. 4 shows that after 9 days of treatment, the triglyceride fraction (TG) in the hexane extract was drastically reduced, and the free fatty acid fraction (FA) virtually disappeared. A reduction in TG and FA was also observable in the $HCCl_3$:MeOH extract after 4 days of treatment.

These results indicate that topical application of triacetin effectively reduces skin surface lipids in the rat. The effect was not obvious after 4 days of treatment, but became clear after 9 days. Analysis by thin layer chromatography indicated that the reduction was mainly in TG and FA fractions of the skin of the treated animals.

EXAMPLE 3

Adult male Sprague-Dawley rats weighing 240–280 g were fed Purina Chow ad lib and kept in individual cages. On day 1, the hair on the back of the animals was clipped with a hair clipper and the back was washed with hexane. The animals were then divided into control and experimental groups.

Topical Treatment with Test Compounds

The control group was not treated with any topical agent. The experimental groups were treated topically with tributyrin, tricaproin and tricaprylin each day for 14 days. The triglycerides were directly pipetted onto an area of approximately 60 to 75 cm² on the back where the hair had been clipped. The application was once daily.

Extraction of Lipids

On day 14, the animals were killed by asphyxiation in $CO_2$. The skin in the back was immediately removed and mounted on the lipid extractor. The area of skin extracted was 28.3 cm². The accumulated lipids on the surface were first extracted six times with 10 ml hexane to remove neutral lipids. The skin was then extracted six times with 10 ml of $CHCl_3$:$CH_3OH$ (2:1) to remove polar lipids. The neutral lipid and polar lipid extracts were pooled separately and filtered through glasswool and filter paper to remove dirt and tissue debris. The solvent was removed by evaporation and the residues were dried at 100° C. overnight. The weight of the residue was determined on an analytical balance.

Hydrolysis of Neutral Lipids

The lipid residue from the hexane extract was hydrolyzed with 3 ml of 1 N KOH in methanol at 100° C. At the end of 2 hours, the hydrolysate was acidified with 6 N HCl. The lipids were extracted three times with 6 ml dichloromethane and the pooled extracts were washed three times with water. The solvent was then removed under a jet of $N_2$ and the residue dried at 100° C. overnight. The weight of the residue was determined on an analytical balance.

In control experiments after hydrolysis and acidification, 30 mg of tricaprylin yielded a residue of 0.5 mg, while 20.6 mg of tripalmitin yielded a residue of 19.1 mg.

The Appearance of Skin and Hair

Rats treated with tricaproin and tricaprylin up to 2 g daily, displayed no visible abnormality of skin or hair growth.

Reduction of Neutral Lipids

The neutral lipids from both control animals and animals treated with the triglycerides were subjected to alkaline hydrolysis. The results are shown in Table I. C4, C6 and C8, respectively, refer to tributyrin, tricaproin and tricaprylin, respectively.

TABLE I

|  | Neutral Lipids* | % Decrease |
|---|---|---|
| Control | 15.74±2.48[5] |  |
| C4 2 g/d | 15.0±3.6[2] | 10.4 |
| C6 1 g/d | 12.0±2.7[3] | 23.8 |
| 2 g/d | 10.6±1.7[2] | 32.7 |
| C8 .5 g/d | 10.25±1.5 (4) | 34.9 |
| 1 g/d | 9.05±1.0[6] | 42.5 |
| 2 g/d | 8.30±1.3[4] | 47.3 |

*The Values are weights in mg per 28.3 cm² of skin. Values of neutral lipids were obtained after removal of contaminating $C_4$, $C_6$ or $C_8$ by hydrolysis. The hydrolysates were acidified and extracted with dichloromethane.

These results indicate that tributyrin ($C_4$) is slightly effective at a 2 g/day level in reducing the neutral lipids in rat skin after a period of treatment of two weeks. Tricaproin ($C_6$) and tricaprylin ($C_8$) on the other hand were effective even at a level as low as 1 g/day and 0.5 g/day respectively.

EXAMPLE 4

When applied topically to rats, trioctanoin reduced the skin surface lipids. This is demonstrated in the following experiment.

Adult Male Sprague-Dawley rats weighing 280–320 g were fed Purina Chow ad lib and kept in individual cages. The hair on the back was clipped with a hair clipper and the back was washed with hexane. The experimental animals were then treated with 0.5, 1 or 2 g of trioctanoin by applying the oil once daily for two weeks to approximately 60–75 cm² of the back where the hair had been clipped. The animals were killed and the skin removed and mounted on a special skin lipid extractor. The area extracted was 28.3 cm². The accumulated neutral lipids on the skin surface were extracted six times with 10 ml hexane. The residual trioctanoin was removed by hydrolysis in 1 N KOH. After acidification and extraction with dichloromethane, the solvent was evaporated under a stream of $N_2$. The weight of residue in mg is presented in the Table II below. The number in parenthesis indicates number of animals. In control experiments, after the hydrolysis of 30.0 mg trioctanoin, the weight of octanoic acid in the dichloromethane extract was 0.5 mg.

ing the same regimen of tricaprylin to one side of his face and Retin A to the other side according to the directions specified on the package, the tricaprylin side improved more rapidly and to a greater extent. A middle aged woman with mild seborrhea, acne, and very sensitive skin found that tricaprylin applied as above greatly improved her condition and was nonirritating.

The triglycerides of the present invention may be employed in a variety of dosage forms. Thus, they may be made up into gels, solutions, lotions or creams. Typical dosage forms of these types are given below.

GELS
% by Weight

| Ingredient | Ex. 6 | Ex. 7 | Ex. 8 | Ex. 9 | Ex. 10 | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|---|---|---|---|---|
| Triacetin | 50 | 50 | — | — | — | — | — | — | — | — | 50 | — | — | — | — |
| Tributyrin | — | — | 50 | 50 | — | — | — | — | — | — | — | 50 | — | — | — |
| Tricaproin | — | — | — | — | 50 | 50 | — | — | — | — | — | — | 50 | — | — |
| Tricaprylin | — | — | — | — | — | — | 50 | 50 | — | — | — | — | — | 50 | — |
| Trioctanoin | — | — | — | — | — | — | — | — | 50 | 50 | — | — | — | — | 50 |
| Mineral Oil | 38 | 40 | 38 | 40 | 38 | 40 | 38 | 40 | 38 | 40 | 38 | 40 | 38 | 40 | 38 |
| Cabosil | 12 | 10 | 12 | 10 | 12 | 10 | 12 | 10 | 12 | 10 | — | — | — | — | — |
| Microthene (Polyethylene) | — | — | — | — | — | — | — | — | — | — | 12 | 10 | 12 | 10 | 12 |

SOLUTIONS
% by Weight

| Ingredient | Ex. 21 | Ex. 22 | Ex. 23 | Ex. 24 | Ex. 25 | Ex. 26 | Ex. 27 |
|---|---|---|---|---|---|---|---|
| Triacetin | 10 | 50 | — | — | — | — | — |
| Tributyrin | — | — | 50 | 10 | — | — | — |
| Tricaproin | — | — | — | — | 10 | — | — |
| Tricaprylin | — | — | — | — | — | 50 | — |
| Trioctanoin | — | — | — | — | — | — | 10 |
| Ethyl Alcohol | QS 100% | QS 100% | QS 100% | QS 100% | QS 100% | QS 100% | QS 100% |

TABLE II

| Rats | Neutral Lipids in Skin Surface | % of Decrease |
|---|---|---|
| Control | 17.45±0.2(2) | |
| Treated | | |
| 0.5 g/day | 10.25±1.5(4) | 41.3 |
| 1 g/day | 6.9±0.8(3) | 60.5 |
| 2 g/day | 6.4±0.9(2) | 63.4 |

EXAMPLE 5

In preliminary clinical tests, the patients were instructed to clean their skin thoroughly with soap and water and then apply 1 gm of tricaprylin to the face 2X/day. In one teenage girl, pimples on the face underwent marked regression in 2–3 days. Another teenage girl showed marked improvement over the same time interval and rated the treatment as very effective and equal to the marketed product, Retin A (retinoic acid). In one male teenager, the improvement in his facial acne after 2 weeks was gauged excellent; in this individual, the response to tricaprylin was considered by the subject and his parents to be much better than that seen previously to Retin A. In a further teenage boy apply-

LOTIONS
% by Weight

| Ingredient | Ex. 28 | Ex. 29 | Ex. 30 | Ex. 31 | Ex. 32 | Ex. 33 |
|---|---|---|---|---|---|---|
| Tributyrin | 50 | — | — | 50 | — | — |
| Tricaproin | — | 50 | — | — | — | 50 |
| Tricaprylin | — | — | 50 | — | 50 | — |
| Arlacel 186 | 4 | — | — | — | — | — |
| Arlacel 83 | — | 10 | — | — | — | — |
| Preservative | QS | QS | QS | QS | QS | QS |
| Tween 60 | — | — | 3 | — | 3 | 10 |
| Atmol 84 | — | — | — | 10 | — | — |
| Water | 46 | 40 | 47 | 40 | 47 | 40 |

CREAMS
% by Weight

| Ingredient | Ex. 34 | Ex. 35 | Ex. 36 | Ex. 37 | Ex. 38 | Ex. 39 |
|---|---|---|---|---|---|---|
| Tributyrin | 50 | — | — | 50 | — | — |
| Tricaproin | — | 50 | — | — | 50 | — |
| Tricaprylin | — | — | 50 | — | — | 50 |
| Arlacel 83 | 5 | 10 | 5 | — | — | — |
| Beeswax | 2 | — | 2 | 2 | — | 5 |
| Ceresin | — | 5 | — | — | 2 | — |
| Arlacel 60 | — | — | — | 5 | — | 5 |
| Tween 60 | — | — | — | — | 10 | — |
| Preservative | QS | QS | QS | QS | QS | QS |

-continued

| | CREAMS % by Weight | | | | | |
|---|---|---|---|---|---|---|
| Ingredient | Ex. 34 | Ex. 35 | Ex. 36 | Ex. 37 | Ex. 38 | Ex. 39 |
| Water | 43 | 35 | 43 | 43 | 38 | 40 |

What is claimed is:

1. A method for treating an area of living skin from which sebum is secreted at an excessive rate to reduce the rate of sebum production from said area of skin which comprises coating said skin area with a triglyceride product comprising at least about 10% by weight and up to about 100% by weight of a triglyceride or a mixture of triglycerides for a time sufficient and in a therapeutically sufficient amount to reduce the rate of sebum production; said triglyceride or triglycerides being of the formula:

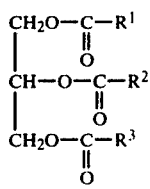

in which $R^1$, $R^2$ and $R^3$ are the same and are straight chain or branched chain saturated or unsaturated aliphatic hydrocarbon radicals containing 1 to 20 carbon atoms.

2. The method according to claim 1 in which said triglyceride product is applied at least once a day for a period of at least nine days.

3. The method according to claim 1 in which the triglyceride or triglycerides employed are such that $R^1$, $R^2$ and $R^3$ are saturated alkyl radicals having 1 to 9 carbon atoms.

4. The method according to claim 1 in which the triglyceride or triglycerides employed are such that $R^1$, $R^2$ and $R^3$ in said formula each have from 10 to 20 carbon atoms.

5. The method according to claim 1 in which the triglyceride product employed contains a mixture of triglycerides in which $R^1$, $R^2$ and $R^3$ in said formula are each radicals containing 7 to 10 carbon atoms.

6. The method according to claim 1 in which the triglyceride or triglycerides employed are such that $R^1$, $R^2$ and $R^3$ in said formula are each branched chain aliphatic hydrocarbon radicals.

7. The method according to claim 1 in which the triglyceride or triglycerides employed are such that $R^1$, $R^2$ and $R^3$ in said formula are each saturated alkyl radicals having 3 to 9 carbon atoms.

8. The method according to claim 1 in which the triglyceride or triglycerides are applied at the daily dosage levels of at least about 0.5 gms/day of triglyceride or triglycerides.

9. The method according to claim 8 in which the triglyceride is triacetin.

10. The method according to claim 8 in which the triglyceride is tributyrin.

11. The method according to claim 8 in which the triglyceride is tricaprylin.

12. The method according to claim 8 in which the triglyceride is tricaproin.

13. The method according to claim 1, wherein said excess rate of sebum secretion in said skin area is associated with acne.

14. The method according to claim 1, wherein said excess rate of sebum secretion in said skin area is associated with seborrhea.

* * * * *